United States Patent
Cavan et al.

(10) Patent No.: US 9,703,207 B1
(45) Date of Patent: Jul. 11, 2017

(54) SYSTEM AND METHOD FOR REDUCING DYNAMIC RANGE IN IMAGES OF PATTERNED REGIONS OF SEMICONDUCTOR WAFERS

(75) Inventors: Daniel L. Cavan, Woodside, CA (US); Grace Chen, Los Gatos, CA (US)

(73) Assignee: KLA-Tencor Corporation, Milpitas, CA (US)

(*) Notice: Subject to any disclaimer, the term of this patent is extended or adjusted under 35 U.S.C. 154(b) by 731 days.

(21) Appl. No.: 13/544,480

(22) Filed: Jul. 9, 2012

Related U.S. Application Data

(60) Provisional application No. 61/505,640, filed on Jul. 8, 2011.

(51) Int. Cl.
- *G03B 27/68* (2006.01)
- *G01N 21/95* (2006.01)
- *G03F 7/20* (2006.01)

(52) U.S. Cl.
CPC ..... *G03F 7/70275* (2013.01); *G01N 21/9501* (2013.01)

(58) Field of Classification Search
USPC .............................. 355/67, 52, 35
See application file for complete search history.

(56) References Cited

U.S. PATENT DOCUMENTS

| | | | |
|---|---|---|---|
| 5,587,832 A | 12/1996 | Krause | |
| 5,617,203 A * | 4/1997 | Kobayashi | G01N 21/95623 250/550 |
| 6,060,224 A * | 5/2000 | Sweatt | G02B 26/0841 250/492.2 |
| 6,566,627 B2 * | 5/2003 | Brandinger | A61F 9/00804 219/121.69 |
| 6,844,927 B2 | 1/2005 | Stokowski et al. | |
| 6,867,424 B2 * | 3/2005 | Kurosawa | G01N 21/9501 250/216 |
| 6,894,834 B2 | 5/2005 | Mann et al. | |
| 7,292,330 B2 | 11/2007 | Saunders et al. | |
| 7,330,265 B2 | 2/2008 | Kurosawa et al. | |
| 7,535,563 B1 * | 5/2009 | Chen | G01N 21/4788 356/237.1 |
| 7,538,868 B2 * | 5/2009 | Shen | G03F 9/7011 356/243.1 |
| 7,869,024 B2 | 1/2011 | Urano et al. | |
| 8,736,831 B2 * | 5/2014 | Ramachandran | G01N 21/9501 356/237.1 |

(Continued)

*Primary Examiner* — Deoram Persaud
(74) *Attorney, Agent, or Firm* — Suiter Swantz pc llo

(57) ABSTRACT

The present invention includes generating illumination, providing a spatial light modulator (SLM) configured to selectably illuminate one or more portions of a surface of a wafer using the generated illumination, receiving a sets of wafer pattern data indicative of one or more patterns of the wafer, translating the wafer along a direction, selectably controlling a pixel configuration of the SLM to control an illumination pattern on the surface of the wafer, a first pixel configuration illuminating a first set of regions of the wafer at an illumination level, an additional pixel configuration illuminating an additional set of regions at an additional illumination level, wherein a pixel pattern of the SLM based on the received sets of wafer pattern data is configured to move across a surface of the SLM synchronously with the pattern of the translated wafer, and detecting illumination from the surface of the wafer.

26 Claims, 6 Drawing Sheets

(56) References Cited

U.S. PATENT DOCUMENTS

| | | | |
|---|---|---|---|
| 8,743,165 B2* | 6/2014 | Sandstrom | B23K 26/032 219/121.68 |
| 2001/0045690 A1* | 11/2001 | Brandinger | B23K 26/032 264/400 |
| 2002/0159044 A1* | 10/2002 | Mei | G03F 7/70275 355/67 |
| 2004/0004699 A1* | 1/2004 | Kanatake | G03F 7/70291 355/45 |
| 2004/0075882 A1* | 4/2004 | Meisburger | G03F 7/70216 359/290 |
| 2006/0007436 A1* | 1/2006 | Kurosawa et al. | 356/237.4 |
| 2006/0176542 A1* | 8/2006 | Muro | G01N 21/6458 359/290 |
| 2008/0144025 A1* | 6/2008 | Vollrath | G01N 21/9501 356/300 |
| 2008/0230863 A1* | 9/2008 | Gautier et al. | 257/437 |
| 2008/0231939 A1* | 9/2008 | Gluckstad | G02B 21/06 359/298 |
| 2010/0039630 A1* | 2/2010 | Michaloski | G03F 7/70275 355/67 |
| 2010/0127431 A1* | 5/2010 | Sandstrom | G06K 17/00 264/400 |
| 2010/0231862 A1* | 9/2010 | Itoh et al. | 353/31 |
| 2011/0242544 A1* | 10/2011 | Stroessner | G03F 1/84 356/496 |
| 2012/0026478 A1* | 2/2012 | Chen | G03F 7/70275 355/53 |
| 2012/0264066 A1* | 10/2012 | Chen | G03F 7/70275 430/322 |
| 2013/0050803 A1* | 2/2013 | Stowe | G03F 7/70275 359/292 |
| 2016/0085156 A1* | 3/2016 | Markle | G03F 7/2051 430/322 |

* cited by examiner

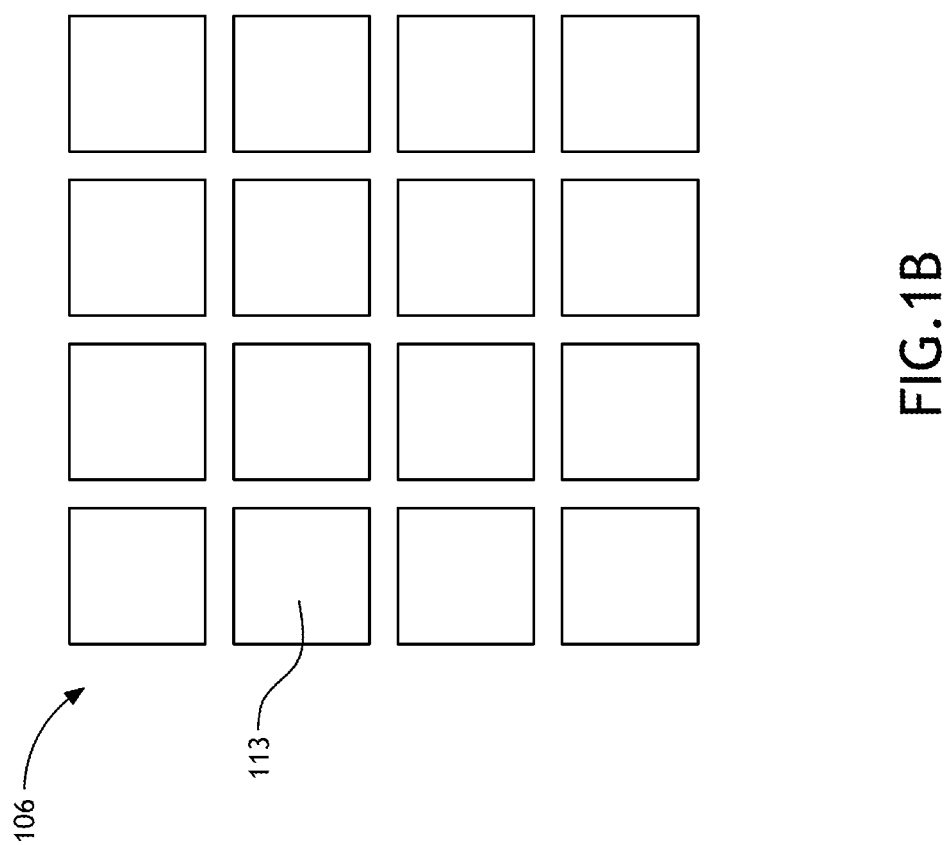

SYSTEM AND METHOD FOR REDUCING DYNAMIC RANGE IN IMAGES OF PATTERNED REGIONS OF SEMICONDUCTOR WAFERS

CROSS-REFERENCE TO RELATED APPLICATION

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

RELATED APPLICATIONS

For purposes of the USPTO extra-statutory requirements, the present application constitutes a regular (non-provisional) patent application of United States Provisional Patent Application entitled DYNAMIC STRUCTURED ILLUMINATION (DSI), naming Daniel L. Cavan and Grace Chen, as inventors, filed Jul. 8, 2011 Application Ser. No. 61/505,640.

TECHNICAL FIELD

The present invention generally relates to semiconductor wafer inspection, and more particularly to a system and method for reducing dynamic range in images acquired using an inspection system.

BACKGROUND

As the dimensions of semiconductor devices and components continue to decrease, the demand for enhanced semiconductor wafer inspection capabilities will continue to increase. One manner in which semiconductor wafer inspection procedures may be improved is through the reduction of dynamic range during semiconductor wafer imagery acquisition. The reduction of dynamic range in inspection imagery data allows for improved defect detection sensitivity during wafer inspection process. In addition, the reduction of dynamic range in inspection imagery data may aid in eliminating common side effects attributed to high dynamic range semiconductor wafer inspection. The side effects include ghosting, flaring, or ringing produced in the imaging optics of an inspection system.

Traditional methods of dynamic range reduction include the saturation of portions of an image obtained from a semiconductor device in order to acquire adequate sensitivity in the darker (array) portions of the substrate. This method does not allow for optimum inspection sensitivity in saturated areas of the wafer. In order to partially compensate for this shortfall, systems and users commonly perform two or more passes, at different illumination levels, over the wafer.

Another commonly utilized methodology includes the reduction in global illumination such that the entirety of a given wafer is illuminated at levels below the various saturation levels, but also below an optimal illumination level for any given device features. In addition, in settings where the illumination of a given illumination source is optimized for darker regions of a wafer pattern, the inspection sensitivity in these dark regions becomes compromised due to the high levels of unwanted light from brighter regions.

The deficiencies described above reduce wafer fabrication throughput and cost of ownership. It would therefore be desirable to provide a system and method, which cures the deficiencies of the prior art.

SUMMARY

An apparatus suitable for providing reduced dynamic range in patterned images is disclosed. In one aspect, the apparatus may include, but is not limited to, an illumination source; a set of illumination optics configured to direct light from the illumination source to a wafer disposed on a sample stage via an illumination path, wherein the sample stage is configured to translate the wafer along a selected direction at a selected rate; a spatial light modulator (SLM) disposed along the illumination path and configured to receive at least a portion of light emanating from the illumination source, the SLM further configured to selectably illuminate one or more portions of a surface of the wafer; an additional set of illumination optics configured to direct light emanating from a surface of the SLM to a surface of the wafer; a detector configured to detect light emanating from the surface of the wafer; a control system communicatively coupled to the SLM, the control system configured to: receive one or more sets of wafer pattern data indicative of one or more patterns of the wafer; and selectably control a pixel configuration of the SLM based on the received one or more sets of wafer pattern data in order to control an illumination pattern on the surface of the wafer, wherein a first pixel configuration illuminates a first set of regions of the wafer at a selected illumination level, wherein an additional pixel configuration illuminates at least an additional set of regions of the wafer at a selected additional illumination level, wherein a pixel pattern of the SLM based on the received one or more sets of wafer pattern data is configured to move across a surface the SLM substantially synchronously with the pattern of the translated wafer.

A method suitable for providing reduced dynamic range in patterned images is disclosed. In one aspect, the method may include, but is not limited to, generating light utilizing an illumination source; providing a spatial light modulator (SLM) configured to selectably illuminate one or more portions of a surface of a wafer using the generated light, the SLM disposed in an illumination pathway defined by the illumination source and the surface of the wafer; receiving one or more sets of wafer pattern data indicative of one or more patterns of the wafer; translating the wafer along a selected direction at a selected rate using a sample stage; selectably controlling a pixel configuration of the SLM in order to control an illumination pattern on the surface of the wafer, wherein a first pixel configuration illuminates a first set of regions of the wafer at a selected illumination level, wherein an additional pixel configuration illuminates at least an additional set of regions of the wafer at a selected additional illumination level, wherein a pixel pattern of the SLM based on the received one or more sets of wafer pattern data is configured to move across a surface the SLM substantially synchronously with the pattern of the translated wafer; and detecting light emanating from the surface of the wafer.

It is to be understood that both the foregoing general description and the following detailed description are exemplary and explanatory only and are not necessarily restrictive of the invention as claimed. The accompanying drawings, which are incorporated in and constitute a part of the specification, illustrate embodiments of the invention and together with the general description, serve to explain the principles of the invention.

BRIEF DESCRIPTION OF THE DRAWINGS

The numerous advantages of the disclosure may be better understood by those skilled in the art by reference to the accompanying figures in which:

FIG. 1B is a topview of a micro-mirror array of a spatial light modulator device, in accordance with one embodiment of the present invention.

DETAILED DESCRIPTION OF THE INVENTION

Reference will now be made in detail to the subject matter disclosed, which is illustrated in the accompanying drawings.

Figure 1A:
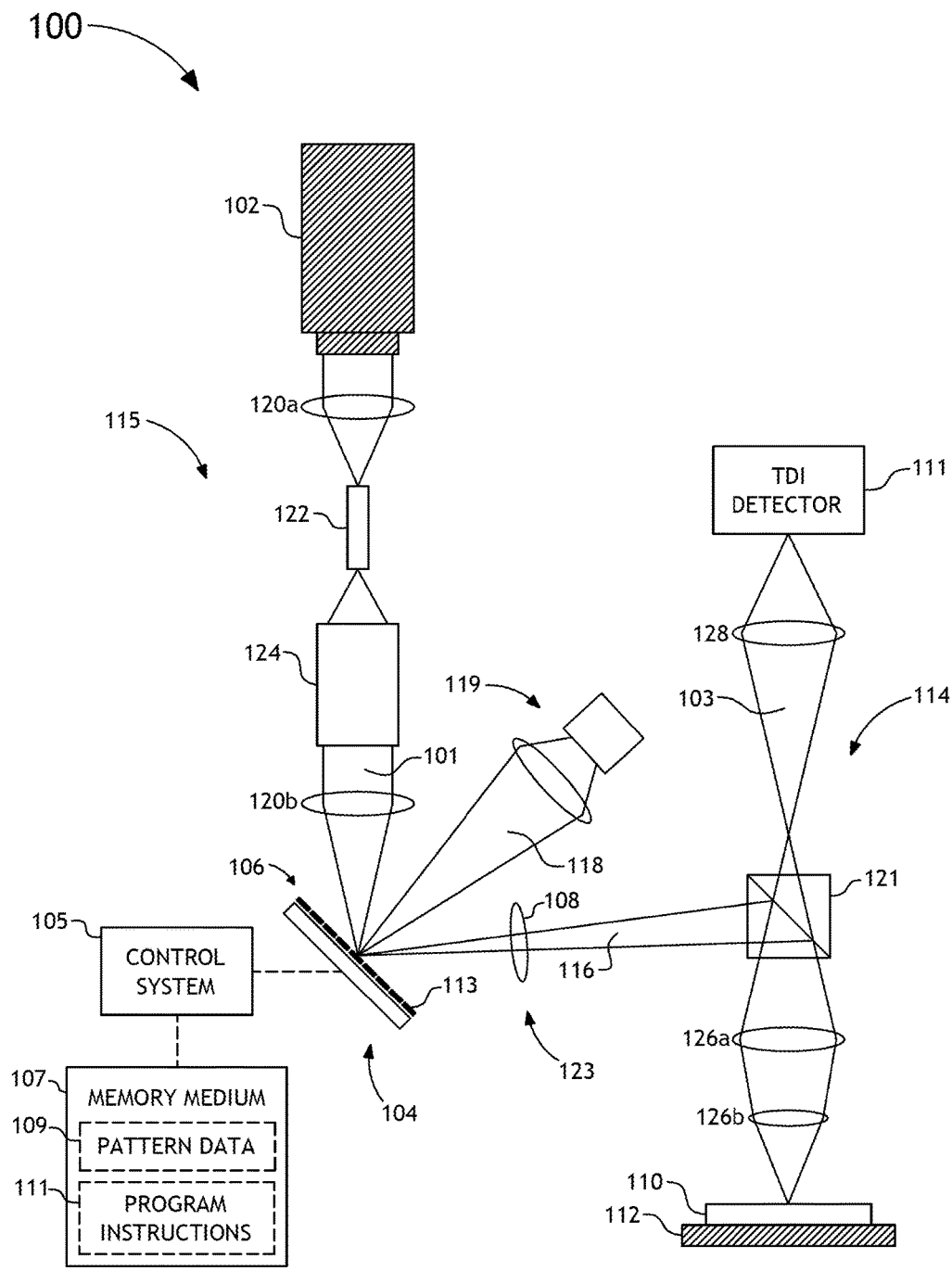
FIG. 1A is a block diagram view of a system for reducing dynamic range in patterned images, in accordance with one embodiment of the present invention.
Figure 1C:
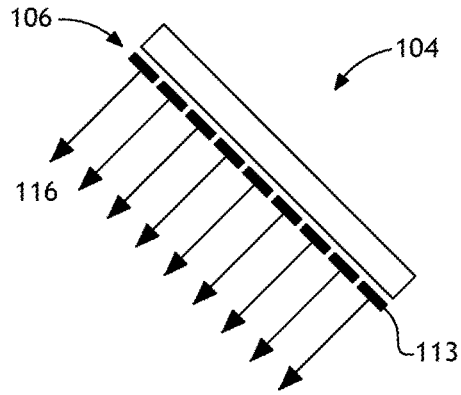
FIG. 1C is a conceptual view of a micro-mirror array of a spatial light modulator device in at a first time, in accordance with one embodiment of the present invention.
Figure 1D:
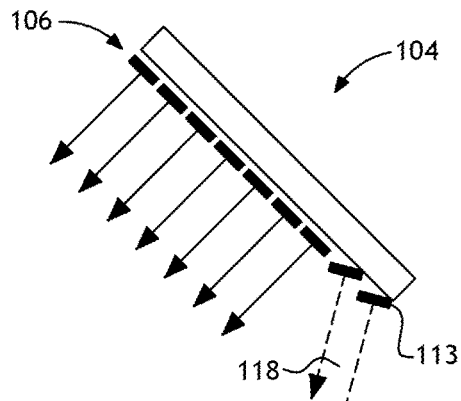
FIG. 1D is a conceptual view of a micro-mirror array of a spatial light modulator device in at a second time, in accordance with one embodiment of the present invention.
Figure 1E:
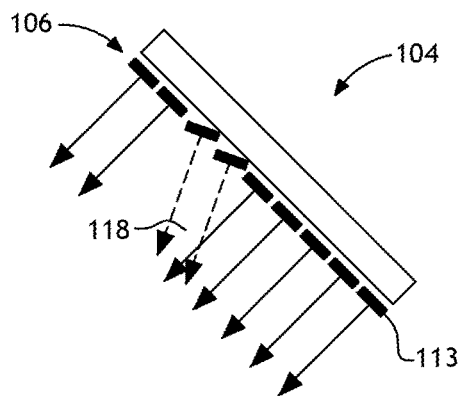
FIG. 1E is a conceptual view of a micro-mirror array of a spatial light modulator device in at a third time, in accordance with one embodiment of the present invention.
Figure 2A:
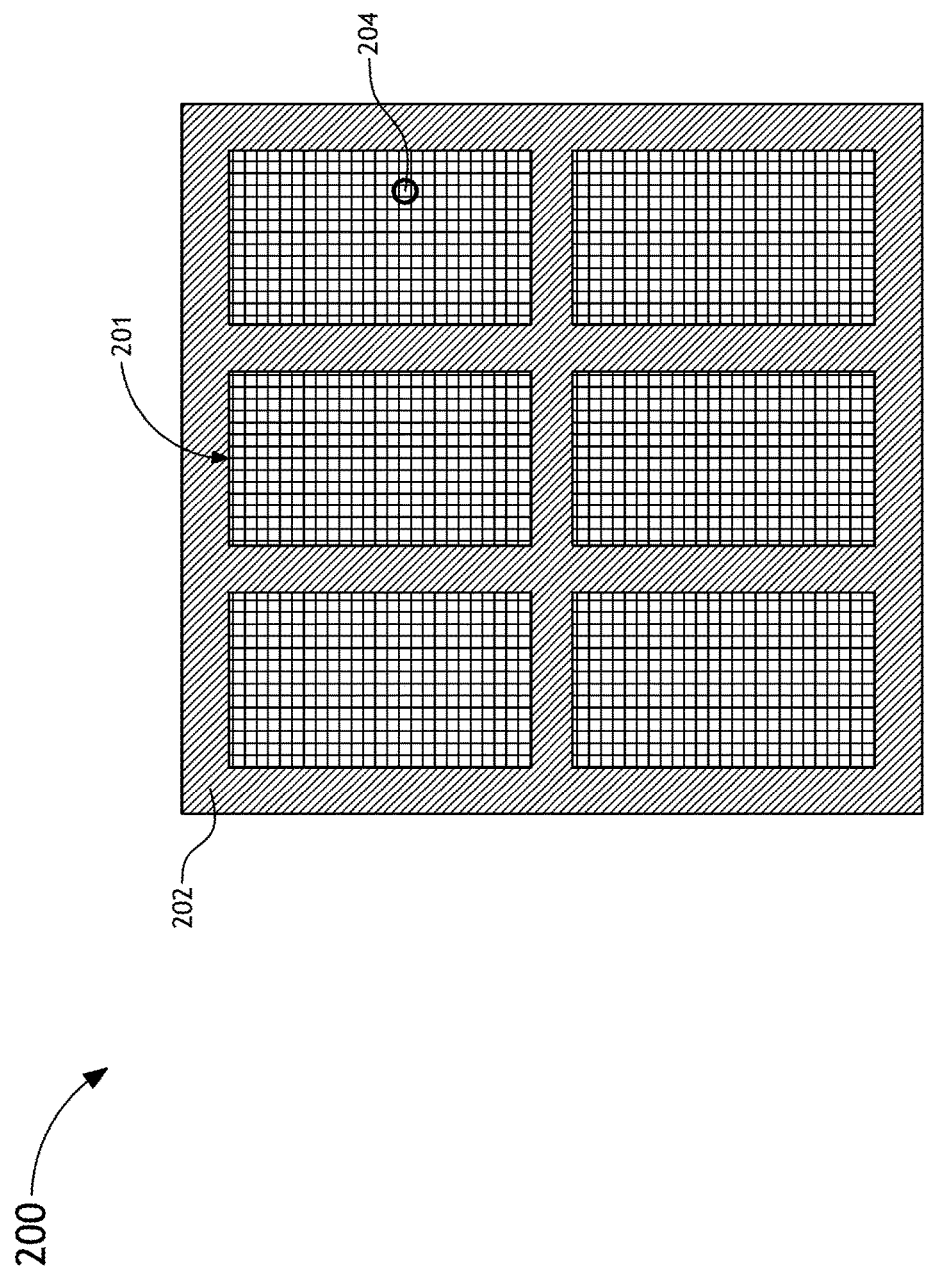
FIG. 2A is a conceptual topview of an array of memory areas of a semiconductor wafer, in accordance with one embodiment of the present invention.
Figure 2B:
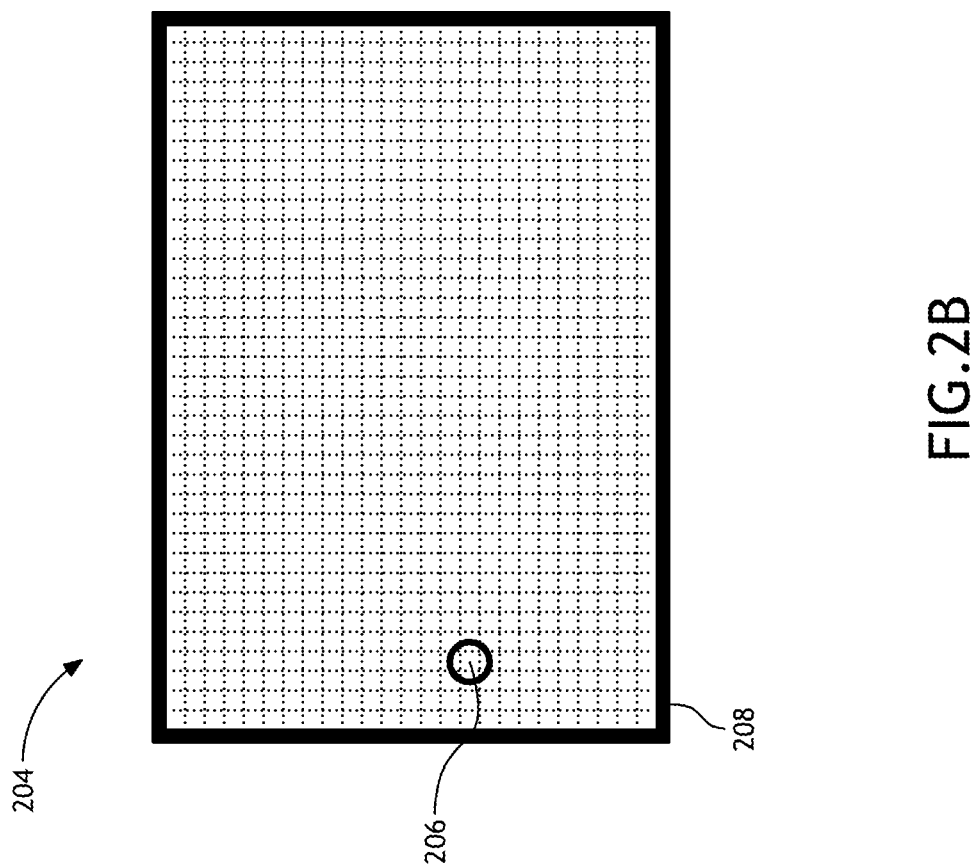
FIG. 2B is a conceptual topview of a memory block of a memory area of a semiconductor wafer, in accordance with one embodiment of the present invention.

Referring generally to FIGS. 1 through 2B, a system 100 for providing reduced dynamic range in patterned images is described in accordance with the present invention. The present invention is directed to a system and method, which produces reduced dynamic range pattern images utilizing a dynamically controlled spatial light modulator (SLM) disposed in the illumination path of an optical system of an inspection system. The SLM or a communicatively coupled control system is programmed with wafer pattern data indicative of pattern data associated with an inspected wafer in question. Using the wafer pattern data, the control system (or the SLM itself) may dynamically control the pixel configuration of the SLM. Even further, the dynamic control of the SLM may allow a given pixel pattern corresponding with the pattern(s) of a semiconductor wafer device to move across a surface of the SLM synchronously with the pattern of the translated wafer. It is further recognized that the reduction in dynamic range helps reduce negative impacts caused by high dynamic range imagery data, such as, but not limited to, ghosting, flaring and ringing.

Referring now to FIGS. 1A through 1E, the system 100 suitable for providing reduced dynamic range in patterned images is described in accordance with the present invention. The system 100 may include an illumination source 102, a set of illumination optics 115 configured to direct illumination along an illumination path 101 towards a wafer 110, a spatial light modulator (SLM) 104 disposed along the illumination path 101 and configured to selectably illuminate one or more portions of the surface of the wafer 110. The system 100 further includes a set of additional illumination optics 123 configured to direct illumination reflected from a micro-array surface 106 of the SLM 104 to the surface of the wafer 110, a translation stage 112 configured to translate the wafer 110 along a selected direction, and a detector 111 (e.g., time delay integration device) configured to collect light emanating from the surface of the wafer 110. In a further aspect, the system 100 includes a control system 105 communicatively coupled to the SLM 104. The control system 105 is configured to perform a pixel level assignment in the SLM 104 such that light incident on the pixels, or "elements," of the microarray of the SLM 104 is in either a reflection mode or a deflection mode, based on the wafer geometry. In this regard, the control system 105, in a first configuration, may direct incident illumination along one direction, while, in a second (or third, fourth, and etc.) configuration, may direct incident illumination along a second direction.

In one aspect of the present invention, the SLM 104 is positioned in an illumination field plane. As such, the optical configuration of the system 100 may include a homogenizer 122 and a set of field relay optics 124. The field relay optics 124 are positioned at the exit of the homogenizer 122 and are optically coupled to the SLM 104. It is recognized herein that placement of the SLM 104 in the illumination path 101 aids in avoiding waveform distortion.

In one embodiment of the present invention, the SLM 104 of the present invention may include any SLM known in the art of spatial light modulation. For example, the SLM 104 may include a reflective-based digital mirror device (DMD). In another example, the SLM 104 may include a diffractive-based micro-mirror enhanced micro-imaging (MEMI) device. In a further embodiment, it is recognized that deep ultraviolet (DUV) compatible SLM devices may be utilized within the context of the present invention.

In another embodiment of the present invention, the set of illumination optics 115 of system 100 may include any illumination optics known in the art. For example, the illumination optics 115 may include, but are not limited to, one or more lenses (e.g., lenses 120a and 120b), one or more filters, one or more mirrors, or one or more beam splitters. In another embodiment, the additional set of illumination optics 123 of the system 100 may include any optics known in the art suitable for directing illumination emanating from the surface of the SLM 104 to the surface of the wafer 110. For example, the additional illumination optics 123 may include, but are not limited to, one or more lenses (e.g., lens 108), one or more filters, one or more mirrors, or one or more beam splitters (e.g., lens 121).

In another embodiment, the system 100 may include a set of collection optics 114 configured to collect and direct light emanating from the surface of the wafer 110 to the TDI detector 111 along a collection pathway 103. The set of collection optics 114 of system 100 may include any collection optics known in the art. For example, the collection optics 114 may include, but are not limited to, one or more lenses (e.g., lens 128), one or more filters, one or more mirrors, or one or more beam splitters.

In a preferred embodiment, as shown in FIG. 1A, a lens 120 may focus light from an illumination source 102 into homogenizer 122. The field relay optics 124 may couple the output of the homogenizer to the surface 106 of the SLM 104. Based on the received wafer pattern data 109, the control system 105 may act to establish a dynamic pixel configuration, which moves across the surface of the SLM 104 synchronously with the motion of the wafer 110, which will be discussed in greater detail throughout the present disclosure. Light reflected from "ON" state pixels is reflected along path 116 to beam splitter 121 and to the surface of the wafer 110. In turn, light reflected from the wafer 110 may be transmitted along the collection pathway 103 to the one or more TDI detectors 111. In contrast, light deflected from "OFF" state pixels may be directed along path 118 and to a beam dump 119.

In another embodiment of the present invention, the illumination source 102 of the present invention may include any illumination source known in the art. In one embodiment, the illumination source 102 may include a narrowband light source. It should be recognized that any known narrowband light source is suitable for implementation in the present invention. For example, the illumination source 102 may include, but is not limited to, one or more laser light sources. For instance, the illumination source 102 may include, but is not limited to, a diode-pumped solid state (DPSS) laser. In another embodiment, the illumination source 102 may include a broadband light source. For example, the illumination source 102 may include, but is not limited to, a halogen light source (HLS). For instance, the halogen light source may include, but is not limited to, a tungsten based halogen lamp. In another example, the illumination source 102 may include a xenon arc lamp. Further, it is recognized that the spectrum of the output of a given broadband source may be narrowed to a desired level (e.g., 10 nm). Those skilled in the art should recognize that there exist a variety of settings wherein a broadband source may be utilized in the context of the present invention. As such, the description provided above should not be interpreted as limiting, but merely as an illustration.

The system 100 of the present invention may be configured as a dark-field inspection system or a bright-field inspection system. In this regard, the system 100 may be configured in a flood illumination configuration, a line illumination system, or a spot scanning system In a further aspect of the present invention, the control system 105 may receive one or more sets of wafer pattern data indicative of one or more patterns of the wafer 110. For example, the control system 105 may receive one or more sets of wafer pattern data upon recipe setup. In another example, the control system 105 may receive one or more sets of wafer pattern data in the form of computer aided drawing (CAD) data acquired during the design or manufacturing of the devices of the wafer 110. In a further embodiment, received wafer pattern data 109 may be stored in a memory 107 (e.g., permanent memory, RAM, solid state memory, optical memory, magnetic memory, and the like). The stored wafer pattern data 109 may then be accessed by a processor (not shown) of the control system 105 in order to control the communicatively coupled SLM 104, as described in greater detail throughout the present disclosure. As shown in FIGS. 2A and 2B, the wafer pattern data 109 may include, but is not limited to, the pattern of the memory array areas 201, the logic areas 202, and the page breaks 208 of a device of the wafer 110. It is noted herein that the listing above is not limiting and should be interpreted merely as illustrative of types of device features of a wafer 110 suitable for application in the present invention.

In a further aspect of the present invention, the control system 105 may selectably control a pixel configuration of the SLM 104 based on the received one or more sets of wafer pattern data 109 in order to control an illumination pattern on the surface of the wafer 110. In this regard, a first pixel configuration of the SLM may illuminate a first set of regions of the wafer at a first selected illumination level, while a second pixel configuration may illuminate a second set of regions of the wafer at a second selected illumination level. In a general sense, an Nth pixel configuration of the SLM may illuminate an Nth set of regions of the wafer 110 at an Nth illumination level. In a further aspect, the control system 105 may control the SLM 104 in order to move a pixel pattern of the SLM 104 (i.e., the pattern of the reflective state of the micro-array reflective or diffractive elements of the SLM 104), based on the received wafer pattern data 109, across a surface 106 of the SLM 104 substantially synchronously with the pattern of the translated wafer 110.

For example, a control system 105 may establish and control a first pixel configuration in the micro-array surface 106 of the SLM 104, arranged to match the received pattern of one or more memory array areas 201 of the wafer. In this regard, the first pixel configuration may be used to illuminate the one or more memory array areas 201 of a semiconductor wafer 110 at a 100% illumination by moving the first pixel configuration across the surface 106 of the SLM synchronously with the motion of the wafer 110. In addition, the control system 105 may establish and control a second pixel configuration in the micro-array surface 106 of the SLM 104, arranged to match the received pattern of the logic areas 202 and/or page breaks 208 of the semiconductor wafer 110. In this regard, the first pixel configuration may be used to illuminate the memory array areas 201 of a semiconductor wafer 110 at a 100% illumination and the second pixel configuration may be used to illuminate the logic areas 202 and/or page breaks 208 at an illumination levels much lower than 100%. For example, the second pixel configuration may be used to illuminate the logic areas 202 and/or page breaks 208 at illuminations levels of approximately 10% illumination. The pixel configuration of the elements 113 of the SLM 104 change synchronously with the motion of the wafer 110, with the manner in which the pixel configuration changes being based on the received wafer pattern data 109. In this sense, the micro-array surface 106 of the SLM 104 is controlled dynamically using the control system 105 in a manner that forms a moving "pattern" (corresponding with the received wafer pattern data and moving synchronously with the wafer 110 motion), which is formed by the combination of the first pixel configuration and at least a second configuration. By programming the control system 105 (or the SLM 104 itself) with the pattern of the memory array areas 201 and moving this pattern across the micro-array surface 106 of the SLM 104 synchronously with the motion of the wafer 110 relative to the additional illumination optics 108, the memory array areas 201 may be illuminated at near 100% illumination, while the logic areas 202 and/or page break areas 208 may be illuminated at illumination levels much less than 100% (e.g., 10%).

In a further aspect of the invention, the intensity modulation (i.e., the modulation of illumination levels) observed at the surface of the wafer 110 may be achieved by turning the second pixel configuration (e.g., pixel configuration corresponding with logic areas 202 and/or page break areas 208 of wafer 110) of the SLM 104 to an "OFF" position for a selected portion of time of the integration interval of the TDI detector 111. In one aspect, the ON-state corresponds to a direction of the micro-mirror elements 113 of the surface 106 of the SLM 104 suitable for reflecting light from the surface of the elements 113 to the optics element 108 and onto the surface of the wafer 110. In another aspect, the OFF-state corresponds to a direction of the micro-mirror elements 113 suitable for reflecting light from the surface of the elements 113 to a region outside of the numerical aperture (NA) of the set of optics 108. In this regard, while in the ON-state, the micro-mirror elements 113 of the SLM 104 act to reflect light from the illumination source 102 onto the surface of the wafer 110, while in the OFF-state, the micro-mirror elements of the SLM 104 act to reflect light from the illumination source 102 in a direction outside of the NA of the collection optics 108 used to direct light to the wafer 110.

FIGS. 1C through 1E depict a conceptual view of the movement of a pre-programmed wafer pattern across the surface 106 of the SLM 104, in accordance with one embodiment of the present invention. In this regard, at a first time (FIG. 1C), the surface normals of the micro-array elements 113 of the micro-array surface 106 may all be directed along a first direction 116 corresponding with the ON-state (i.e., directed toward the wafer 110) of the SLM 104. At a second time, depicted in FIG. 1D, a portion of the elements 113 may have surface normals directed along a second direction 118 corresponding with the OFF-state (i.e., directed along a direction outside the NA of collection optics 108) of the SLM 104, with the remainder of the elements 113 having surface normals directed along the ON-state direction 116. At a third time, depicted in FIG. 1E, another portion of the elements 113 may have surface normals directed along a second direction 118 corresponding with the OFF-state, with the remainder of the elements 113 having surface normals directed along the ON-state direction 116. This depiction displays the manner in which a given pattern may be "moved" across the surface 106 of the SLM 104. For instance, the elements in FIG. 1D and FIG. 1E configured in the OFF-state may correspond to logic areas 202 and/or page breaks 208 of the wafer 110, allowing for small levels of illumination (relative to the memory array areas) to be directed onto the logic areas 202 and/or page breaks 208 of the wafer 110 as it translates along a given direction. In this manner, any pattern corresponding to a pattern of a device structure of the wafer 110 may be moved across the surface 106 of the SLM 104 in synchronicity with the movement of the pattern on the wafer 110. It is further noted that the above pattern movement depiction is not limiting and should be interpreted as merely illustrative. It is anticipated that any patterned wafer feature may be implemented in the context of the present invention and it is further recognized that the pattern may (and likely will) form a 2-dimensional pattern on the surface 106 of the SLM 104, which may "move" across the surface 106 of the SLM 104.

It is further recognized that the elements 113 of the SLM 104 may provide for variable light exposure to a given area of the wafer 110 by programming number of mirror elements 113 of the SLM 104 that are in the ON-state relative to the number of elements 113 in the OFF-state as the wafer 110 transits the imaged field of view.

It is noted herein that the achievable modulation level (i.e., difference between ON and OFF illumination states) is a function of a variety of factors. These factors include, but are not limited to, the number of TDI integration stages, the TDI line rate, and the frequency response of the SLM 104. For example, utilizing a 1024 stage TDI operating at approximately 1 ms integration time, applicant has found that a 100:1 dynamic range compression is achievable using a 1 MHz SLM device. It is further recognized that faster SLM devices may allow for greater levels of modulation. In addition, slower TDI integration speeds may also provide for greater dynamic range compression.

It is further noted that the number of pixels 113 of the SLM 104 required for adequate performance is approximately equal to the object field size divided by illumination spot size. For example, for a 266 nm band operating in a dark field (0.65 NA) with a 1.2 mm field the approximate required size of the corresponding SLM device 104 of the system 100 is 4000 by 1000. Applicant notes that the provided estimate is not limiting is provided merely for illustrative purposes.

Moreover, the illumination attenuation factor utilized for the logic areas 202 and/or page break areas 208 may be used to re-scale the "bright" areas of the final image back to their original brightness relative to the "dark" array areas. This procedure aids in avoiding the multiple problems associated with high dynamic range images, which include page breaking ringing, ghosting, and sensor cross talk.

It should be recognized that the various steps described throughout the present disclosure may be carried out by a single computer system or, alternatively, a multiple computer system. Moreover, different subsystems of the system 100, such as the SLM 104, may include a computer system suitable for carrying out at least a portion of the steps described above. Therefore, the above description should not be interpreted as a limitation on the present invention but merely an illustration. Further, the one or more computer control systems 105 may be configured to perform any other step(s) of any of the method embodiments described herein.

The one or more computing control systems 105 may include, but are not limited to, a personal computer system, mainframe computer system, workstation, image computer, parallel processor, or any other device known in the art. In general, the term "computing control system" may be broadly defined to encompass any device having one or more processors, which execute instructions from a memory medium 107.

Program instructions 111 implementing methods such as those described herein may be stored on the memory medium and transmitted via a carrier medium. The carrier medium may be a transmission medium such as a wire, cable, or wireless transmission link. The memory medium 107 may include a permanent storage medium such as a read-only memory, a random access memory, a magnetic or optical disk, or a magnetic tape. In an additional aspect, the one or more sets of wafer pattern data 109 received from a wafer pattern data source may be stored in the memory medium 107.

Figure 3:
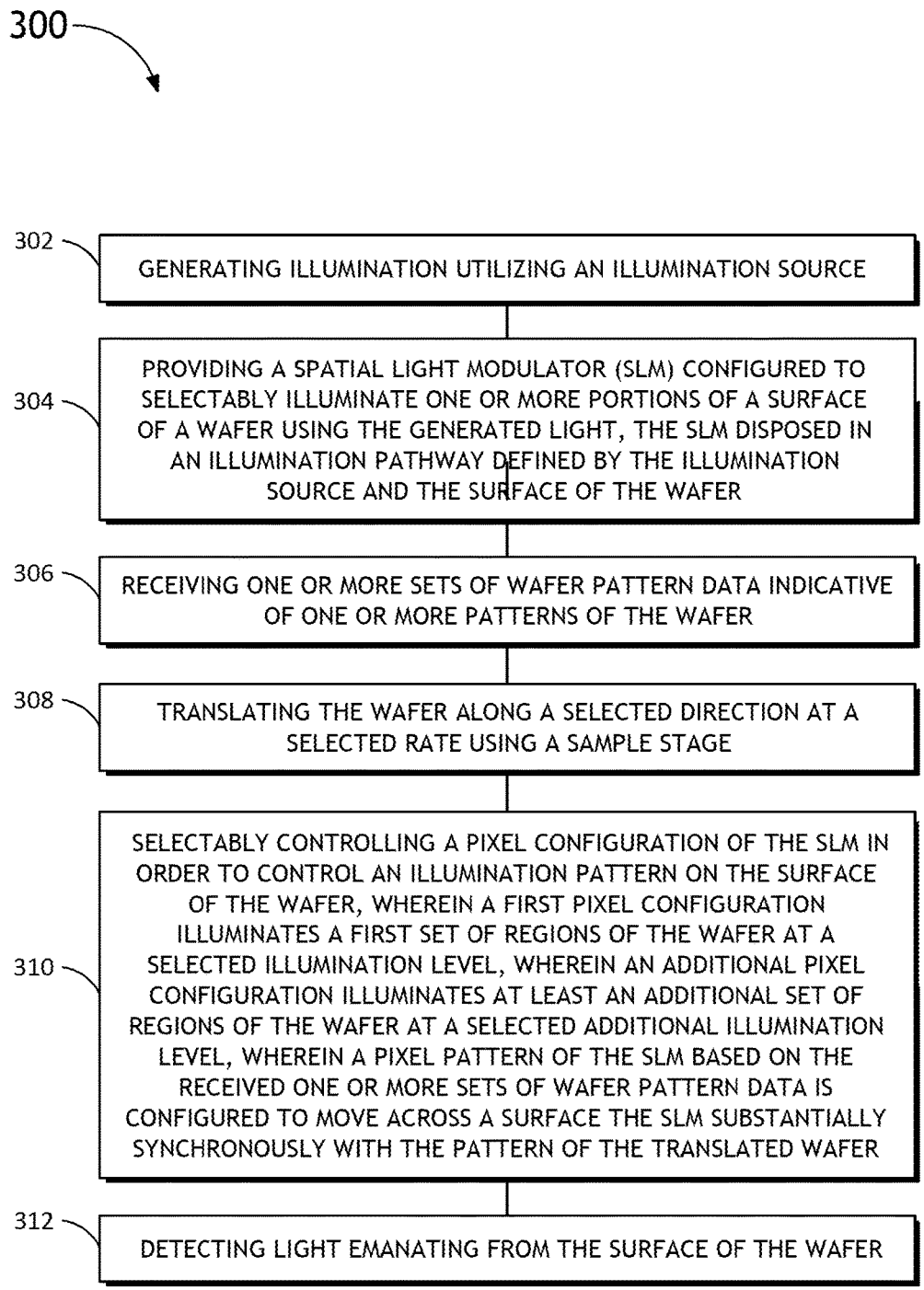
FIG. 3 is a process flow diagram of a method for reducing dynamic range in patterned images, in accordance with one embodiment of the present invention.

FIG. 3 illustrates a process flow 300 suitable for implementation by systems 100 of the present invention. In one aspect, it is recognized that data processing steps of the process flow 300 may be carried out via a pre-programmed algorithm executed by one or more processors of the one or more computer control systems 105.

Step 302 generates a beam of illumination. For instance, one or more laser sources may generate a beam of laser light. Step 304 provides a spatial light modulator (SLM) configured to selectably illuminate one or more portions of a surface of a wafer using the generated illumination. In a further aspect, the SLM is disposed in an illumination pathway defined by the illumination source and the surface of the wafer. For example, the SLM may include, but is not limited to, a reflective-based SLM or a diffractive-based SLM. Step 306 receives one or more sets of wafer pattern data indicative of one or more patterns of the wafer. For example, a control system 105 may receive one or more sets of wafer pattern data. For instance, wafer pattern data (e.g., locations of memory array patterns) may be transmitted to the control system 105 upon recipe setup. In another instance, wafer pattern data may be acquired via CAD data used in the design and manufacturing of a given semiconductor device of the wafer 110. The wafer data 109 may be stored in a memory 107. Step 308 translates the wafer 110 along a selected direction at a selected rate using a sample stage. Step 310 selectably controls a pixel configuration of the SLM 104 in order to control an illumination pattern on the surface of the wafer. In one aspect, a first pixel configuration illuminates a first set of regions of the wafer 110 at a selected illumination level, while an additional pixel configuration illuminates at least an additional set of regions of the wafer 110 at a selected additional illumination level. In a further aspect, a pixel pattern of the SLM 104 based on the received one or more sets of wafer pattern data is configured to move across a surface the SLM 104 substantially synchronously with the pattern of the translated wafer 110. Step 312 detects illumination form the surface of the wafer.

All of the system and methods described herein may include storing results of one or more steps of the method embodiments in a storage medium. The results may include any of the results described herein and may be stored in any manner known in the art. The storage medium may include any storage medium described herein or any other suitable storage medium known in the art. After the results have been stored, the results can be accessed in the storage medium and used by any of the method or system embodiments described herein, formatted for display to a user, used by another software module, method, or system, etc. Furthermore, the results may be stored "permanently," "semi-permanently," temporarily, or for some period of time. For example, the storage medium may be random access memory (RAM), and the results may not necessarily persist indefinitely in the storage medium.

Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "connected", or "coupled", to each other to achieve the desired functionality, and any two components capable of being so associated can also be viewed as being "couplable", to each other to achieve the desired functionality. Specific examples of couplable include but are not limited to physically mateable and/or physically interacting components and/or wirelessly interactable and/or wirelessly interacting components and/or logically interacting and/or logically interactable components.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein.

Although particular embodiments of this invention have been illustrated, it is apparent that various modifications and embodiments of the invention may be made by those skilled in the art without departing from the scope and spirit of the foregoing disclosure. Accordingly, the scope of the invention should be limited only by the claims appended hereto.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes.

Furthermore, it is to be understood that the invention is defined by the appended claims.

What is claimed is:

1. An apparatus suitable for providing reduced dynamic range in patterned images, comprising:
   an illumination source;
   a set of illumination optics configured to direct light from the illumination source to a wafer disposed on a sample stage via an illumination path, wherein the sample stage is configured to translate the wafer along a selected direction at a selected rate;

a spatial light modulator (SLM) disposed along the illumination path and configured to receive at least a portion of light emanating from the illumination source, the SLM further configured to selectably illuminate one or more portions of a surface of the wafer, wherein the SLM is arranged so as to direct light from ON-state pixels of the SLM to the surface of the wafer;

a time delay and integration (TDI) detector configured to detect light emanating from the surface of the wafer;

a control system communicatively coupled to the SLM, the control system configured to:

receive one or more sets of wafer pattern data indicative of one or more patterns of the wafer; and selectably control a pixel configuration of the SLM based on the received one or more sets of wafer pattern data in order to control an illumination pattern on the surface of the wafer, wherein the pixel configuration illuminates a first set of regions of the wafer at a first illumination intensity level, wherein the pixel configuration illuminates at least an additional set of regions of the wafer at an additional illumination intensity level, wherein the additional illumination intensity level is less than the first illumination intensity level, wherein the pixel configuration delivers illumination to the first set of regions and at least the additional set of regions of the wafer in the same inspection mode, wherein the control system turns a set of pixels of the SLM associated with at least the additional set of regions to an OFF position for at least a portion of a TDI integration interval, associated with the first set of regions, of the TDI detector, wherein a pixel pattern of the SLM based on the received one or more sets of wafer pattern data is configured to move across a surface of the SLM substantially synchronously with the wafer as the wafer transits an imaged field of view formed by the illumination optics.

2. The apparatus of claim 1, wherein the control system is configured to perform a calibration procedure in order to compensate for a length of time one or more elements of the SLM is in the OFF position.

3. The apparatus of claim 1, wherein the OFF position comprises:

a position of the one or more pixels suitable for reflecting light from the surface of the SLM to a region outside of a numerical aperture of the set of additional illumination optics.

4. The apparatus of claim 1, wherein the first set of regions comprises:

one or more memory array areas of the wafer.

5. The apparatus of claim 1, wherein the at least an additional set of regions comprises:

at least one of one or more logic areas of the wafer or one or more page break areas of the wafer.

6. The apparatus of claim 1, wherein the illumination optics comprise:

a homogenizer configured to receive illumination from the illumination source; and a set of field relay optics configured to receive illumination emanating from the homogenizer and further configured to generate an illumination field plane suitable for utilization by the SLM.

7. The apparatus of claim 1, wherein the spatial light modulator comprises:

a diffraction-based spatial light modulator.

8. The apparatus of claim 1, wherein the spatial light modulator comprises:

a reflection-based spatial light modulator.

9. The apparatus of claim 1, wherein the spatial light modulator comprises:

a microelectro-mechanical systems (MEMS) spatial light modulator.

10. The apparatus of claim 1, wherein the spatial light modulator comprises:

a liquid crystal spatial light modulator.

11. The apparatus of claim 1, wherein the inspection mode comprises:

a bright field inspection mode.

12. The apparatus of claim 1, wherein the inspection mode comprises:

a dark field inspection mode.

13. The apparatus of claim 1, wherein the illumination source comprises:

one or more lasers.

14. The apparatus of claim 1, wherein the one or more wafers comprise:

one or more semiconductor wafers.

15. A method suitable for providing reduced dynamic range in patterned images, comprising:

generating light utilizing an illumination source;

selectably illuminating one or more portions of a surface of a wafer, with a spatial light modulator (SLM), using the generated light, the SLM disposed in an illumination pathway defined by the illumination source and the surface of the wafer, wherein the SLM is arranged so as to direct light from ON-state pixels of the SLM to the surface of the wafer;

receiving one or more sets of wafer pattern data indicative of one or more patterns of the wafer;

translating the wafer along a selected direction at a selected rate using a sample stage;

detecting light emanating from the surface of the wafer with a time delay and integration (TDI) detector;

selectably controlling a pixel configuration of the SLM in order to control an illumination pattern on the surface of the wafer, wherein the pixel configuration illuminates a first set of regions of the wafer at a first illumination intensity level, wherein the pixel configuration illuminates at least an additional set of regions of the wafer at an additional illumination level, wherein the additional illumination intensity level is less than the first illumination intensity level, wherein the pixel configuration delivers illumination to the first set of regions and at least the additional set of regions of the wafer in the same inspection mode, switching a set of pixels of the SLM associated with at least the additional set of regions to an OFF position for at least a portion of a TDI integration interval, associated with the first set of regions, of the TDI detector, wherein a pixel pattern of the SLM based on the received one or more sets of wafer pattern data is configured to move across a surface of the SLM substantially synchronously with the wafer as the wafer transits an imaged field of view.

16. The method of claim 15, wherein the OFF position comprises:
a position of the one or more pixels suitable for reflecting light from the surface of the SLM to a region outside of a numerical aperture of an additional set illumination collection optics.

17. The method of claim 15, wherein the first set of regions comprises:
one or more memory array areas of the wafer.

18. The method of claim 15, wherein the at least an additional set of regions comprises:
at least one of one or more logic areas of the wafer and one or more page break areas of the wafer.

19. The method of claim 15, further comprising:
homogenizing at least a portion of the generated illumination; and
generating an illumination field plane using the homogenized illumination suitable for utilization by the SLM.

20. The method of claim 15, wherein the spatial light modulator comprises:
a diffraction-based spatial light modulator.

21. The method of claim 15, wherein the spatial light modulator comprises:
a reflection-based spatial light modulator.

22. The method of claim 15, wherein the spatial light modulator comprises:
a microelectro-mechanical systems (MEMS) spatial light modulator.

23. The method of claim 15, wherein the spatial light modulator comprises:
a liquid crystal spatial light modulator.

24. The method of claim 15, wherein the illumination source comprises:
one or more lasers.

25. The method of claim 15, wherein the one or more wafers comprise:
one or more semiconductor wafers.

26. The method of claim 15, wherein the detector comprises:
a time delay integration (TDI) detector.

* * * * *